United States Patent
Al-Khattaf et al.

(10) Patent No.: US 10,583,423 B2
(45) Date of Patent: *Mar. 10, 2020

(54) DUAL CATALYST SYSTEM FOR PROPYLENE PRODUCTION

(71) Applicants: Saudi Arabian Oil Company, Dhahran (SA); King Fahd University of Petroleum & Minerals, Dhahran (SA)

(72) Inventors: Sulaiman Saleh Al-Khattaf, Dhahran (SA); Arudra Palani, Dhahran (SA); Tazul Islam Bhuiyan, Dhahran (SA); Sohel Shaikh, Dhahran (SA); Mohammad Naseem Akhtar, Dhahran (SA); Abdullah M. Aitani, Al-Khobar (SA); Mohammed A. Al-Yami, Dhahran (SA)

(73) Assignees: Saudi Arabian Oil Company, Dhahran (SA); King Fahd University of Petroleum & Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/039,983

(22) Filed: Jul. 19, 2018

(65) Prior Publication Data

US 2018/0326408 A1    Nov. 15, 2018

Related U.S. Application Data

(60) Continuation of application No. 15/398,196, filed on Jan. 4, 2017, now Pat. No. 10,052,618, which is a
(Continued)

(51) Int. Cl.
*B01J 29/06* (2006.01)
*B01J 29/70* (2006.01)
*C07C 6/04* (2006.01)
*C07C 4/06* (2006.01)
*B01J 21/08* (2006.01)
(Continued)

(52) U.S. Cl.
CPC ............. *B01J 29/70* (2013.01); *B01J 8/04* (2013.01); *B01J 21/08* (2013.01); *B01J 23/30* (2013.01); *B01J 29/005* (2013.01); *B01J 29/035* (2013.01); *B01J 29/0308* (2013.01); *B01J 29/0341* (2013.01); *B01J 29/18* (2013.01); *B01J 29/40* (2013.01); *B01J 29/78* (2013.01); *B01J 35/002* (2013.01); *B01J 35/0006* (2013.01); *B01J 35/023* (2013.01); *B01J 35/108* (2013.01); *B01J 35/1019* (2013.01); *B01J 35/1023* (2013.01); *B01J 35/1042* (2013.01); *B01J 35/1047* (2013.01); *B01J 35/1061* (2013.01); *B01J 37/0201* (2013.01); *C01B 37/02* (2013.01); *C07C 4/06* (2013.01); *C07C 6/04* (2013.01); *C07C 6/06* (2013.01); *B01J 29/0358* (2013.01); *B01J 29/48* (2013.01); *B01J 35/109* (2013.01); *B01J 35/1057* (2013.01); *B01J 2229/20* (2013.01); *C07C 2521/08* (2013.01); *C07C 2523/30* (2013.01); *C07C 2529/03* (2013.01); *C07C 2529/035* (2013.01); *C07C 2529/40* (2013.01); *C07C 2529/48* (2013.01);
(Continued)

(58) Field of Classification Search
CPC . B01J 29/40; B01J 29/48; B01J 29/005; B01J 29/0308; B01J 29/0341; B01J 29/035; B01J 29/0358; B01J 2229/20; B01J 35/0006; B01J 35/108; B01J 35/1042; B01J 35/1047; B01J 35/109; B01J 35/1061; B01J 35/1057; B01J 35/1019; B01J 35/1023; B01J 35/023; B01J 37/0201; C07C 2529/40; C07C 2529/48; C07C 2529/03; C07C 2529/035; C07C 2529/108; C07C 2521/08
USPC ........ 502/63, 64, 69, 71; 422/187, 600, 630, 422/631, 632, 633, 634
See application file for complete search history.

(56) References Cited

U.S. PATENT DOCUMENTS 3,442,821 A    5/1969 Hilfman
3,546,313 A    12/1970 Banks
(Continued)

FOREIGN PATENT DOCUMENTS

CN    101531558 A    9/2009
CN    102177223 A *  9/2011
(Continued)

OTHER PUBLICATIONS

Hu et al., "Highly Active Doped Mesoporous KIT-6 Catalysts for Metathesis of 1-Butene and Ethene to Propene: The Influence of Neighboring Environment of W Species", J. Phys. Chem., ACS Publication, 2013, pp. 26385-26395.*
Kumar et al., "Performance of Nano Crystalline H-ZSM-5 As Additive in FCC Catalyst : A Review", International Journal of Research in Engineering and Technology, vol. 03 Special Issue, May 2014, pp. 481-485.*
Yuan Guimei et al., Machine translation of CN 104370676, Feb. 2015.*
Machine translation claims of CN 102177223 A, Sep. 2011.*
Machine translation description of CN 102177223 A. Sep. 2011.*
Examination Report pertaining to GCC Application No. 2016/31672 dated Sep. 13, 2018.
(Continued)

Primary Examiner — Elizabeth D Wood
(74) Attorney, Agent, or Firm — Dinsmore & Shohl, LLP (57) ABSTRACT

Embodiments of processes for producing propylene utilize a dual catalyst system comprising a mesoporous silica catalyst impregnated with metal oxide and a mordenite framework inverted (MFI) structured silica catalyst downstream of the mesoporous silica catalyst, where the mesoporous silica catalyst includes a pore size distribution of at least 2.5 nm to 40 nm and a total pore volume of at least 0.600 $cm^3/g$, and the MFI structured silica catalyst has a total acidity of 0.001 mmol/g to 0.1 mmol/g. The propylene is produced from the butene stream via metathesis by contacting the mesoporous silica catalyst and subsequent cracking by contacting the MFI structured silica catalyst.

16 Claims, 2 Drawing Sheets

Related U.S. Application Data division of application No. 15/190,981, filed on Jun. 23, 2016, now Pat. No. 9,884,794.

(60) Provisional application No. 62/188,178, filed on Jul. 2, 2015.

(51) Int. Cl.

| | | |
|---|---|---|
| B01J 23/30 | (2006.01) |
| B01J 29/18 | (2006.01) |
| B01J 35/00 | (2006.01) |
| B01J 35/10 | (2006.01) |
| B01J 35/02 | (2006.01) |
| B01J 29/40 | (2006.01) |
| C01B 37/02 | (2006.01) |
| B01J 8/04 | (2006.01) |
| B01J 29/00 | (2006.01) |
| B01J 29/03 | (2006.01) |
| B01J 29/035 | (2006.01) |
| B01J 29/78 | (2006.01) |
| B01J 37/02 | (2006.01) |
| C07C 6/06 | (2006.01) |
| B01J 29/48 | (2006.01) |

(52) U.S. Cl.
CPC ...... C07C 2529/70 (2013.01); C07C 2529/78 (2013.01); Y02P 20/52 (2015.11)

(56) References Cited

U.S. PATENT DOCUMENTS

| | | | |
|---|---|---|---|
| 3,586,731 A | | 6/1971 | Heckelsberg |
| 3,702,886 A | | 11/1972 | Argauer et al. |
| 4,024,201 A | | 5/1977 | Takahashi |
| 4,071,471 A | | 1/1978 | Banks et al. |
| 4,575,575 A | | 3/1986 | Drake et al. |
| 4,609,769 A | * | 9/1986 | Kukes ............... B01J 21/063 585/643 |
| 5,026,935 A | | 6/1991 | Leyshon et al. |
| 5,026,936 A | | 6/1991 | Leyshon et al. |
| 5,191,131 A | | 3/1993 | Takahata et al. |
| 6,207,115 B1 | | 3/2001 | Chodorge et al. |
| 6,538,168 B1 | | 3/2003 | Schwab et al. |
| 6,586,649 B1 | | 7/2003 | Botha et al. |
| 6,646,172 B1 | | 11/2003 | Schwab et al. |
| 6,777,582 B2 | | 8/2004 | Gartside et al. |
| 6,977,321 B1 | | 12/2005 | Dath et al. |
| 7,214,841 B2 | | 5/2007 | Gartside et al. |
| 7,754,647 B2 | | 7/2010 | Schubert et al. |
| 7,754,934 B2 | | 7/2010 | Tsunoda et al. |
| 7,977,522 B2 | | 7/2011 | Takai et al. |
| 8,299,313 B2 | | 10/2012 | Takai et al. |
| 8,324,440 B2 | | 12/2012 | Popp et al. |
| 8,440,874 B2 | | 5/2013 | Ramachandran et al. |
| 8,586,813 B2 | | 11/2013 | Ramachandran et al. |
| 8,722,568 B2 | | 5/2014 | Popp et al. |
| 9,834,497 B2 | | 12/2017 | Shaikh et al. |
| 9,884,794 B2 | | 2/2018 | Al-Khattaf et al. |
| 2003/0176754 A1 | | 9/2003 | Gartside et al. |
| 2004/0254411 A1 | | 12/2004 | Steinbrenner et al. |
| 2005/0014981 A1 | | 1/2005 | Gartside et al. |
| 2006/0293548 A1 | | 12/2006 | Spamer et al. |
| 2007/0038010 A1 | | 2/2007 | Xie et al. |
| 2007/0225478 A1 | | 9/2007 | Querci et al. |
| 2008/0171655 A1 | | 7/2008 | Creyghton et al. |
| 2010/0041930 A1 | | 2/2010 | Gartside et al. |
| 2010/0168487 A1 | | 7/2010 | Sawyer et al. |
| 2010/0234542 A1 | | 9/2010 | Blackborow et al. |
| 2011/0021858 A1 | | 1/2011 | Ramachandran et al. |
| 2011/0152595 A1 | | 6/2011 | Takai et al. |
| 2011/0196185 A1 | | 8/2011 | Krawczyk et al. |
| 2012/0108864 A1 | * | 5/2012 | Gartside ............... C07C 4/06 585/250 |
| 2012/0264990 A1 | | 10/2012 | Nicholas et al. |
| 2012/0283090 A1 | | 11/2012 | Popp et al. |
| 2012/0289617 A1 | | 11/2012 | Wang et al. |
| 2013/0085311 A1 | | 4/2013 | Youn et al. |
| 2013/0165701 A1 | | 6/2013 | Zhou et al. |
| 2013/0245348 A1 | | 9/2013 | Vermeiren et al. |
| 2014/0148629 A1 | | 5/2014 | van Hal et al. |
| 2015/0141721 A1 | | 5/2015 | Choi et al. |
| 2016/0237006 A1 | | 8/2016 | Stoyanova et al. |
| 2017/0001925 A1 | | 1/2017 | Abudawoud et al. |
| 2017/0001926 A1 | | 1/2017 | Shaikh et al. |
| 2017/0001927 A1 | | 1/2017 | Al-Khattaf et al. |
| 2018/0057425 A1 | | 3/2018 | Shaikh et al. |

FOREIGN PATENT DOCUMENTS

| | | |
|---|---|---|
| CN | 102325742 A | 1/2012 |
| CN | 101531558 B | 4/2013 |
| CN | 102325742 B | 7/2014 |
| CN | 104370676 A | 2/2015 |
| DE | 10013253 A1 | 9/2001 |
| EP | 304515 B1 | 12/1991 |
| EP | 0920911 A1 | 6/1999 |
| EP | 2151424 A1 | 2/2010 |
| JP | 2003500190 A | 1/2003 |
| JP | 2012500304 A | 1/2012 |
| WO | 9929805 A1 | 6/1999 |
| WO | 00/71255 A1 | 11/2000 |
| WO | 2006089957 A1 | 8/2006 |
| WO | 2009117128 A1 | 9/2009 |
| WO | 2010019595 A2 | 2/2010 |
| WO | 2008136280 A1 | 7/2010 |
| WO | 2011136983 A1 | 11/2011 |
| WO | 2015055594 A1 | 4/2015 |
| WO | 2017003812 A1 | 1/2017 |
| WO | 2017003817 A1 | 1/2017 |
| WO | 2017003821 A1 | 1/2017 |

OTHER PUBLICATIONS

Arudra et al., "Silicalite-1 as Efficient Catalyst for Production of Propene from 1-Butene", ACS Catalysis, 2014, 4205-4212, 4, American Chemical Society.

Awayssa et al., "Modified HZSM-5 as FCC Additive for Enhancing Light Olefins Yield from Catalytic Cracking of VGO", Applied Catalysis A: General, 2014, 172-183, 477.

Balcar, et al., "Mesoporous molecular sieves as advanced supports for olefin metathesis catalysts", Coordination Chemistry Reviews 257, 2013, pp. 3107-3124, Czech Republic.

Barrett et al., "The Determination of Pore Volume and Area Distributions in Porous Substances. I. Computations from Nitrogen Isotherms", J. Am. Chem. Soc., 1951, 373-380, 73(1).

Beck et al., "A New Family of Mesoporous Molecular Sieves Prepared with Liquid Crystal Templates", J. Am. Chem. Soc., 1992, 10834-10843, 114, American Chemical Society.

Bhuiyan et al., "Kinetics Modelling of 2-Butene Metathesis Over Tungsten Oxide Containing Mesoporous Silica Catalyst", The Canadian Journal of Chemical Engineering, 2014, 1271-1282. 92.

Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 224-234, 467, Elsevier B.V.

Bin Hu, et al., "Highly Active Doped Mesoporous KIT-6 Catalysts for Metathesis of 1-Butene and Ethene to Propene: The Influence of Neighboring Environment of W Species", The Journal of Physical Chemistry, ACS Publication, 2013 American Chemical Society, pp. 26385-26395, USA.

Daniell et al., Enhanced Surface Acidity in Mixed Alumina-Silicas: A Low-Temperature FTIR Study:, 2000, 196, 247-260, Elsevier.

Do et al., "Zeolite Nanoclusters Coated onto the Mesopore Walls of SBA-15", J. Am. Chem. Soc., 2004, 14324-14325, 126, American Chemical Society.

International Search Report and Written Opinion dated Nov. 11, 2016 pertaining to International Application No. PCT/US2016/039025.

(56) References Cited

OTHER PUBLICATIONS

International Search Report and Written Opinion dated Sep. 14, 2016 pertaining to International Application No. PCT/US2016/039012.
International Search Report and Written Opinion dated Sep. 27, 2016 pertaining to International Application No. PCT/US2016/0038967.
International Search Report and Written Opinion dated Sep. 14, 2016 pertaining to International Application No. PCT/US2016/039013.
Jermy et al., "Utilization of ZSM-5/MCM-41 Composite as FCC Catalyst Additive for Enhancing Propylene Yield from VGO Cracking", J. Porous Mater, 2012, 499-509, 19, Springer.
Kawai et al., "Metaethesis of Halogen-Containing Olefin Over Re2O7/Al2O3 Catalyst Promited with Alkylmetal as a Cocatalyst", Journal of Molecular Catalysis A: Chemical, 1998, 133, 51-59.
Kumar et al., "Performance of Nano Crystalline H-ZSM-5 As Additive in FCC Catalyst: A Review", International Journal of Research in Engineering and Tehnology, May 2014, vol. 3, pp. 481-485.
Lwin et al., "Olefin Metathesis by Supported Metal Oxide Catalysts", ACS Catalysis, 2014, 2505-2520, 4, American Chemical Society.
Office Action pertaining to U.S. Appl. No. 15/190,950 dated Sep. 27, 2017.
Office Action pertaining to U.S. Appl. No. 15/190,964 dated Nov. 2, 2017.
Quignard et al., "Aryloxide Ligands in Metathesis of Olefins and Olefinic Esters: Catalytic Behaviour ofW(OAr)2Cl4 by SnMe4, Sn(n-Bu)4, Pb(n-Bu)4, MgNp2: synthesis of W(OAr)2Cl2(CHCMe3)(OR2) and W(OAr)2Cl(CHCMe3)(CH2CMe3)(OR2)", Journal of Molecular Catalysis, 1986, 36, 13-29.
Ruihua Gao, et al., "High-activity, single-site mesoporous WO3-MCF materials for the catalytic epoxidation of cycloocta-1,5-diene with aqueous hydrogen peroxide", Journal of Catalysis, 256, 2008, pp. 259-267, China.
Wang et al., "Synthesis and Structure of Silicalite-1/SBA-15 Composites Prepared by Carbon Templating and Crystallization", Journal of Materials Chemistry, 2007,4265-4273,17, The Royal Society of Chemistry 2007.
Wang et al., "Effect of Support Nature on WO3/SiO2 Structure and Butene-1 Metathesis", Applied Catalysis A: General, 2003, 25-37, 250, Elsevier B.V.
Zhao et al., "Effect of Tungsten Oxide Loading on Metathesis Activity of Ethene and 2-Butene Over WO3/SiO2 Catalysts" Transition Met Chem, 2009, 621-27, 34, Springer.
International Preliminary Report on Patentability dated Jan. 11, 2018—PCT/US2016/039012.
International Preliminary Report on Patentability dated Jan. 2, 2018—PCT/US2016/039012.
Non-Final Office Action pertaing to U.S. Appl. No. 15/398,196 dated Jan. 9, 2018.
Puriwat, et al., "Elucidation of the basicity dependence of 1-butene isomerization on MgO/Mg(OH)s catalysts", Catalysis Communications, 2010, pp. 80-85.
"International Search Report and Written opinion dated Mar. 28, 2018, pertaining to International Application No. PCT/US2018/013945, filed Jan. 17, 2018, 9 pages".
U.S. Office Action dated Apr. 20, 2018 pertaining to U.S. Continuation U.S. Appl. No. 15/859,794, filed Jan. 2, 2018.
International Search Report and Written Opinion dated Apr. 24, 2018 pertaining to International Application No. PCT/US2018/014131, filed Jan. 18, 2018.
Notice of Allowance dated Apr. 24, 2018 pertaining to U.S. Appl. No. 15/190,964, filed Jun. 23, 2016.
Election/Restriction Requirement dated May 21, 2018, pertaining to U.S. Appl. No. 15/866,772, filed Jan. 10, 2018.
Korean Office Action pertaining to Korea Application No. 10-2018-7003238 dated May 14, 2018 (English Translation).
Office Action pertaining to U.S. Appl. No. 15/866,800 dated Jun. 29, 2018.
Office Action pertaining to U.S. Appl. No. 15/190,981 dated Apr. 4, 2017.
Office Action pertaining to U.S. Appl. No. 15/866,772 dated Aug. 28, 2018.
Harmse et al., "On the Product Formation in 1-Butene Methathesis over Supported Tungsten Catalysts", Catal. Lett, vol. 137, pp. 123-131, Apr. 2010.
Shaikh et al., "Self-Methathesis of Butenes to Propylene", Catalysis in Petroleum Refining & Petrochemicals, pp. 1-6, Dec. 7-8, 2015.
Debecker et al., "Preparation of Mo03/si02—Al2O3 methathesis catalysts via wet impregnation with different Mo precursors", Journal of Molecular Catalysis A: Chemical , 340, pp. 65-76, 2011.
Wu et al., "Investigation on acidity of zeolites bound with silica and alumina", Studies in Surface Science and Catalysis, 143, pp. 217-225, 2002.
Office Action dated Jan. 31, 2019 pertaining to U.S. Appl. No. 15/866,800, filed Jan. 10, 2018 (34 pg).
Notice of Allowance dated Mar. 5, 2019 pertaining to U.S. Appl. No. 15/866,772, filed Jan. 10, 2018.
Office Action dated Apr. 5, 2019 pertaining to U.S. Appl. No. 15/873,421, filed Jan. 17, 2018, 49 pgs.
Notice of Allowance and Fee(s) Due dated Aug. 29, 2019 pertaining to U.S. Appl. No. 15/859,794, filed Jan. 2, 2018, 22 pgs.
Notice of Allowance and Fee(s) Due dated Sep. 26, 2019 pertaining to U.S. Appl. No. 15/873,421, filed Jan. 17, 2018, 30 pgs.
Office Action dated May 2, 2019 pertaining to U.S. Appl. No. 15/859,794, filed Jan. 2, 2018, 30 pgs.
Office Action dated May 2, 2019 pertaining to U.S. Appl. No. 16/156,634, filed Oct. 10, 2018, 32 pgs.
Notice of Allowance and Fee(s) Due dated May 15, 2019 pertaining to U.S. Appl. No. 16/156,616, filed Oct. 10, 2018, 35 pgs.
U.S. Office Action dated Jun. 14, 2019 pertaining to U.S. Appl. No. 15/866,800, filed Jan. 10, 2018, 38 pgs.
European Search Report for Application No. 19163840.2 dated Aug. 2, 2019.
Chinese Office Action for Application No. 201811179717.1 dated Jun. 13, 2019.
European Search Report for Application No. 16738274.6 dated Aug. 2, 2019.
Office Action dated Jun. 18, 2019 pertaining to Korean Patent Application No. 10-2018-7003251.
Office Action dated Mar. 30, 2019 pertaining to Japanese Patent Application No. 2017-567370.
Decision of Rejection pertaining to Japanese Application No. 2017-567370 dated Sep. 4, 2019.
Examination Report for Application No. GC 2018/34631 dated Aug. 22, 2019.
Office Action dated Nov. 20, 2019 pertaining to U.S. Appl. No. 16/156,634, filed Oct. 10, 2018, 37 pgs.

* cited by examiner

DUAL CATALYST SYSTEM FOR PROPYLENE PRODUCTION

CROSS REFERENCE TO RELATED APPLICATION

This application is a continuation of U.S. patent application Ser. No. 15/398,196 filed Jan. 4, 2017, now U.S. Pat. No. 10,052,618, which is a divisional of U.S. patent application Ser. No. 15/190,981 filed Jun. 23, 2016, now U.S. Pat. No. 9,884,794, which claims the benefit of U.S. Provisional Application Ser. No. 62/188,178 filed Jul. 2, 2015.

TECHNICAL FIELD

Embodiments of the present disclosure generally relate to propylene production via metathesis reactions, and more specifically relate to converting butene to propylene using a dual catalyst system comprising metathesis and cracking catalysts.

BACKGROUND

In recent years, there has been a dramatic increase in the demand for propylene to feed the growing markets for polypropylene, propylene oxide and acrylic acid. Currently, most of the propylene produced worldwide (74 million tons/year) is a by-product from steam cracking units (57%) which primarily produce ethylene, or a by-product from Fluid Catalytic Cracking (FCC) units (30%) which primarily produce gasoline. These processes cannot respond adequately to a rapid increase in propylene demand.

Other propylene production processes contributes about 12% of total propylene production. Among these processes are propane dehydrogenation (PDH), metathesis reactions requiring both ethylene and butene, high severity FCC, olefins cracking and methanol to olefins (MTO). However, propylene demand has exceeded ethylene and gasoline/distillate demand, and propylene supply has not kept pace with this increase in propylene demand.

SUMMARY

Accordingly, ongoing needs exist for improved processes for the selective production of propylene using dual catalyst systems. Embodiments of the present disclosure are directed to propylene production from butenes via a dual catalyst system.

In one embodiment, a process for the production of propylene is provided. The process comprises providing a dual catalyst system comprising: a mesoporous silica catalyst impregnated with metal oxide, and a mordenite framework inverted (MFI) structured silica catalyst downstream of the mesoporous silica catalyst. The mesoporous silica catalyst includes a total pore volume of at least about 0.600 cm$^3$/g, and the MFI structured silica catalyst includes a total acidity of 0.001 mmol/g to 0.1 mmol/g. The process also comprises producing propylene from a stream comprising butene via metathesis and cracking by contacting the stream comprising butene with the dual catalyst system, where the stream comprising butene contacts the mesoporous silica catalyst before contacting the MFI structured silica catalyst.

In another embodiment, a dual catalyst system for producing propylene from butene is provided. The dual catalyst system comprises a metathesis catalyst zone and a cracking catalyst zone downstream of the metathesis catalyst zone. The metathesis catalyst zone comprises mesoporous silica catalyst impregnated with metal oxide, where the mesoporous silica catalyst includes a pore size distribution of at least 2.5 nm to 40 nm and a total pore volume of at least 0.600 cm$^3$/g. The cracking catalyst zone comprises a mordenite framework inverted (MFI) structured silica catalyst, where the MFI structured silica catalyst includes a, pore size distribution of at least 1.5 nm to 3 nm, and a total acidity of 0.001 mmol/g to 0.1 mmol/g.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

DETAILED DESCRIPTION

Embodiments of the present disclosure are directed to systems and methods for converting a stream comprising butene to a stream comprising propylene via catalyzed metathesis and catalyzed cracking. Specifically, the present embodiments are related to a two-stage catalyst system containing metathesis and cracking catalysts for greater propylene (C$_3$=) production from a butene stream. In operation, the metathesis catalyst is followed by the cracking catalyst to provide a greater yield of propylene, and optionally a greater combined yield of propylene and ethylene.

As shown in the following Formulas 1 and 2, "metathesis" or "self-metathesis" is generally a two-step process: 2-butene isomerization and then cross-metathesis using the metathesis catalyst system. As shown in the following Formula 3, "catalyzed cracking" refers to the conversion of C$_4$-C$_6$ alkenes to propylene and other alkanes and/or alkenes, for example, C$_1$-C$_2$ alkenes.

Formula 1: 2-Butene Isomerization

Formula 2: Cross-Metathesis

Formula 3: Catalytic Cracking

Referring to Formulas 1-3, the "metathesis" and "catalytic cracking" reactions are not limited to these reactants and products; however, Formulas 1-3 provide a basic illustration of the reaction methodology. As shown in Formulas 1 and 2, metathesis reactions take place between two alkenes. The groups bonded to the carbon atoms of the double bond are exchanged between the molecules to produce two new alkenes with the swapped groups. The specific catalyst that is selected for the olefin metathesis reaction may generally determine whether a cis-isomer or trans-isomer is formed, as the coordination of the olefin molecules with the catalyst play an important role, as do the steric influences of the substituents on the double bond of the newly formed molecule.

The present dual catalyst system comprises: a mesoporous silica catalyst, which is a mesoporous silica catalyst support impregnated with metal oxide; and a mordenite framework inverted (MFI) structured silica catalyst downstream of the mesoporous silica catalyst. Various structures are contemplated for the mesoporous silica catalyst support, for example, a molecular sieve. As used in the application, "mesoporous" means that the silica support has a narrow pore size distribution. Specifically, the mesoporous silica catalyst includes a narrow pore size distribution of from about 2.5 nm to about 40 nm and a total pore volume of at least about 0.600 cm$^3$/g. Without being bound by theory, the present pore size distribution and pore volume are sized to achieve better catalytic activity and reduced blocking of pores by metal oxides, whereas smaller pore volume and pore size catalyst systems are susceptible to pore blocking and thereby reduced catalytic activity.

Moreover, utilizing an MFI structured silica catalyst downstream of the mesoporous silica catalyst surprisingly provides the best yield of propylene from a butene stream. The person of ordinary skill in the art would have expected the best yield by first cracking butene to propylene and then cracking any remaining butene via metathesis. However, it was surprisingly found that propylene yield is increased, and additionally the combined yield of propylene and ethylene is increased by placing the MFI structured silica catalyst downstream of the mesoporous silica catalyst.

In one or more embodiments, the pore size distribution of the mesoporous silica catalyst may range from about 2.5 nm to about 40 nm, or about 2.5 nm to about 20 nm, or about 2.5 nm to about 4.5 run, or about 2.5 nm to about 3.5 nm, or about 8 nm to about 18 nm, or about 12 nm to about 18 nm. In further embodiments, the total pore volume may be from about 0.600 cm$^3$/g to about 2.5 cm/g, or about 0.600 cm$^3$/g to about 1.5 cm$^3$/g, or about 0.600 cm$^3$/g to about 1.3 cm$^3$/g, or about 0.600 cm$^3$/g to about 0.800 cm$^3$/g, or about 0.600 cm$^3$/g to about 0.700 cm/g, or about 0.900 cm$^3$/g to about 1.3 cm$^3$/g.

Moreover, while broader ranges are contemplated, the mesoporous silica catalyst may, in one or more embodiments, include a surface area of about 250 meters/gram (m$^2$/g) to about 600 nm/g. In further embodiments, the mesoporous silica catalyst may have a surface area of from about 450 m$^2$/g to about 600 m$^2$/g, or about 250 m$^2$/g to about 350 m$^2$/g, or about 275 m$^2$/g to about 325 m$^2$/g, or about 275 m$^2$/g to about 300 m$^2$/g. Further, the mesoporous silica catalyst may have a total acidity of up to about 0.5 millimole/gram (mmol/g), or about 0.01 mmol/g to about 0.5 mmol/g, or about 0.1 mmol/g to about 0.5 mmol/g, or about 0.3 mmol/g to about 0.5 mmol/g, or about 0.4 mmol/g to about 0.5 mmol/g. Acidity is generally maintained at or less than about 0.5 mmol/g to yield the desired selectivity of propylene and reduced production of undesirable byproducts such as aromatics. Increasing acidity may increase the overall butene conversion; however, this increased conversion may lead to less selectivity and increased production of aromatic byproducts, which can lead to catalyst coking and deactivation.

Furthermore, the mesoporous silica catalyst may have a particle size of from about 20 nm to about 200 nm, or about 50 nm to about 150 nm, or about 75 nm to about 125 nm. In additional embodiments, the mesoporous silica catalyst may have an individual crystal size of about 1 µm to about 100 µm, or about 10 µm to about 40 µm.

Various formulations for the mesoporous silica support, as well as methods of making the formulation, are contemplated. For example, the mesoporous silica catalyst support may be produced via wet impregnation, hydrothermal synthesis, or both. Additionally, the mesoporous silica catalyst support may be characterized by an ordered pore structure. For example, this ordered structure may have a hexagonal array of pores. One suitable embodiment of a mesoporous silica support with a hexagonal pore array may be the Santa Barbara Amorphous (SBA-15) mesoporous silica molecular sieve. Alternatively, another suitable embodiment of a mesoporous silica support is the CARiACT Q-10 (Q-10) spherical catalyst support produced by Fuji Silysia Chemical Ltd.

The catalyst of the metathesis reaction is the impregnated metal oxide of the silica support. The metal oxide may comprise one or oxides of a metal from the Groups 6-10 of the IUPAC Periodic Table. In one or more embodiments, the metal oxide may be an oxide of molybdenum, rhenium, tungsten, or combinations thereof. In a specific embodiment, the metal oxide is tungsten oxide ($WO_3$). It is contemplated that various amounts of metal oxide may be impregnated into the mesoporous silica catalyst support. For example and not by way of limitation, the molar ratio of silica to metal oxide, for example, $WO_3$, is about 5 to about 60, or about 5 to about 15, or about 20 to about 50, or about 20 to about 40, or about 25 to about 35.

Additionally, various silica structures are contemplated for the MFI structured silica catalyst. For example, the MFI structured silica catalyst may include MFI structured aluminosilicate zeolite catalysts or MFI structured silica catalysts free of alumina. As used herein, "free" means less than 0.001% by weight of alumina in the MFI structured silica catalyst. Moreover, it is contemplated that the MFI structured silica catalyst may include other impregnated metal oxides in addition to or as an alternative to alumina. Like the mesoporous silica catalyst, the MFI structured catalysts may have alumina, metal oxides, or both impregnated in the silica support. In addition to or as a substitute for alumina, it is contemplated to include the metal oxides listed prior, specifically, one or more oxides of a metal from Groups 6-10 of the IUPAC Periodic Table, more specifically, metal oxides of molybdenum, rhenium, tungsten, titanium, or combinations thereof.

For the MFI structured aluminosilicate zeolite catalysts, various amounts of alumina are contemplated. In one or more embodiments, the MFI structured aluminosilicate zeolite catalysts may have a molar ratio of silica to alumina of about 5 to about 5000, or about 100 to about 4000, or about 200 to about 3000, or about 1500 to about 2500, or about 1000 to about 2000. Various suitable commercial embodiments of the MFI structured aluminosilicate zeolite catalysts are contemplated, for example, ZSM-5 zeolites such as MFI-280 produced by Zeolyst International or MFI-2000 produced by Saudi Aramco.

Various suitable commercial embodiments are also contemplated for the alumina free MFI structured catalysts. One such example is Silicalite-1 produced by Saudi Aramco.

The MFI structured silica catalyst may include a pore size distribution of from about 1.5 nm to 3 nm, or about 1.5 nm to 2.5 nm. Furthermore, the MFI structured silica catalyst may have a surface area of from about 300 $nm^2/g$ to about 425 $m^2/g$, or about 340 $m^2/g$ to about 410 $m^2/g$. Additionally, the MFI structured silica catalyst may have a total acidity of from about 0.001 mmol/g to about 0.1 mmol/g, or about 0.01 mmol/g to about 0.08 mmol/g. The acidity is maintained at or less than about 0.1 mmol/g in order to reduce production of undesirable byproducts such as aromatics. Increasing acidity may increase the amount of cracking; however, this increased cracking may also lead to less selectivity and increased production of aromatic byproducts, which can lead to catalyst coking and deactivation.

In some cases, MFI structured silica catalyst may be modified with an acidity modifier to adjust the level of acidity in the MFI structured silica catalyst. For example, these acidity modifiers may include rare earth modifiers, phosphorus modifiers, potassium modifiers, or combinations thereof. However, as the present embodiments are focused on reducing the acidity to a level at or below 0.1 mmol/g, the present structured silica catalyst may be free of acidity modifier, such as those selected from rare earth modifiers, phosphorus modifiers, potassium modifiers, or combinations thereof. As used herein, "free of acidity modifiers" means less than less than 0.001% by weight of acidity modifier in the MFI structured silica catalyst.

Further, the MFI structured silica catalyst may have a pore volume of from about 0.1 $cm^3/g$ to about 0.3 $cm^3/g$, or about 0.15 $cm^3/g$ to about 0.25 $cm^3/g$. Additionally, the MFI structured silica catalyst may have an individual crystal size ranging from about 10 nm to about 40 μm, or from about 15 μm to about 40 μm, or from about 20 μm to about 30 μm. In another embodiment, the MFI structured silica catalyst may have an individual crystal size in a range of from about 1 μm to about 5 μm.

Moreover, various amounts of each catalyst are contemplated for the present dual catalyst system. For example, it is contemplated that the ratio by volume of metathesis catalyst to cracking catalyst may range from about 5:1 to about 1:5, or about 2:1 to about 1:2, or about 1:1.

In operation, a product stream comprising propylene is produced from a butene containing stream via metathesis conversion by contacting the butene stream with the dual catalyst system. The butene stream may comprise 2-butene, and optionally comprises one or more isomers, such as 1-butene, trans-2-butene, and cis-2-butene. The present discussion centers on butene based feed streams; however, it is known that other $C_1$-$C_6$ components may also be present in the feed stream.

The mesoporous silica catalyst is a metathesis catalyst which facilitates isomerization of 2-butene to 1-butene followed by cross-metathesis of the 2-butene and 1-butene into a metathesis product stream comprising propylene, and other alkenes/alkanes such as pentene. The MFI structured silica catalyst, which is downstream of the metathesis catalyst, is a cracking catalyst which produces propylene from $C_4$ or $C_5$ olefins in the metathesis product stream, and may also yield ethylene.

It is contemplated that the metathesis catalyst and the cracking catalyst are disposed in one reactor or multiple reactors. For example, it may be desirable to use separate reactors for the metathesis and cracking catalysts when they operate at different environmental conditions, including temperature and pressure. Regardless of whether one or multiple reactors contain the dual catalysts, the dual catalyst system will have a metathesis catalyst zone or section and a downstream cracking catalyst zone or section. For example, the mesoporous silica metathesis catalyst may be located in the top part of the reactor and the MFI structured silica cracking catalyst may be disposed in the bottom part of the reactor, assuming the reactant stream enters the top portion of the reactor. For example, each catalyst may be positioned as discrete catalyst beds. Moreover, it is contemplated that the two catalysts of the dual catalyst system may be in contact with one another or separated. However, if the metathesis catalyst and cracking catalyst are in contact, it is desirable that the metathesis catalyst is still disposed upstream of the cracking catalyst. The catalysts can be used in the same reactor or with different reactors arranged in series. Alternatively, it is contemplated that the metathesis catalyst (mesoporous silica catalyst) is disposed in a first reactor and the cracking catalyst (MFI structured silica catalyst) is disposed in a separate second reactor downstream of the first reactor. In specific embodiments, there is a direct conduit between the first reactor and second reactor, so that the cracking catalyst can directly crack the product of the butene metathesis reaction. Various systems which incorporate the catalyst system are contemplated. For details regarding such systems, co-pending Saudi Aramco U.S. Application No. 62/188,052 entitled Systems and Methods of Producing Propylene is incorporated by reference in its entirety.

Various methods of making the catalysts used in the dual catalyst system are contemplated. Specifically, the processes of wet impregnation and hydrothermal synthesis may be utilized; however, other catalyst synthesis techniques are also contemplated.

Various operating conditions are contemplated for the contacting of the butene stream with the dual catalyst system. For example, the butene stream may contact the dual catalyst system at a space hour velocity of about 10 to about 10,000 $h^{-1}$, or about 300 to about 1200 $h^{-1}$. Moreover, the butene stream may contact the catalyst system at a temperature of from about 200 to about 600° C., or about 300 to about 600° C. Furthermore, the butene stream may contact the catalyst system at a pressure from about 1 to about 30 bars, or about 1 to about 10 bars.

Optionally, the dual catalyst system may be pretreated prior to metathesis and/or cracking. For example, the dual catalyst system may be pretreated with $N_2$ for about 1 hour to about 5 hours before metathesis at a temperature of at least about 400° C., or at least about 500° C.

The product stream yielded by the dual catalyst system may have at least an 80 mol. % conversion of butene and a propylene yield in mol. % of at least 40%. In a further embodiment, the product stream may have at least an 85 mol. % conversion of butene and a propylene yield in mol. % of the at least 45%. Moreover, the product stream may have at least a 15 mol. % yield of ethylene, or at least a 20 mol. % yield of ethylene. In yet another embodiment, the product stream may have at least 45 mol. % yield of propylene, or at least about a 50 mol. % yield of propylene.

Moreover, the product stream may comprise less than 1 about wt % aromatics, or less than about 5 wt % of alkanes and aromatics. Without being bound by theory, in some embodiments it may be desirable that the aromatics and alkanes yield be low as it indicates coke formation, which may result in catalyst deactivation.

EXAMPLES

The following examples show the preparation of various catalysts which are used in a combination as in the present dual catalysts.

Example 1

Preparation of W-SBA-15(30)

Sodium tungstate was used as the source of tungsten ion for the synthesis of W-SBA-15 by direct hydrothermal method. In a typical synthesis of W-SBA-15, tungsten was incorporated into the framework of mesoporous support SBA-15 depending upon the Si/W molar ratio. Pluronic® 123 (P123) was dissolved in HCl and tetraethylorthosilicate (TEOS) was added with vigorous stirring. Then, a calculated amount of sodium tungstate solution was added to the solution and stirred at 95° C. for 3 days under hydrothermal conditions. The resultant solid was filtered, dried and calcined at 550° C. for 5 hours. The catalysts obtained in this way were identified as W-SBA-15(30), where 30 represents the molar ratio of silicon to tungsten (Si/W). The molar ratio of the gel composition is 1 $SiO_2$:0.3-0.6 $WO_3$:0.0167 P123: 5.82 HCl:190 $H_2O$.

Example 2

Preparation of Silicalite-1

In a typical synthesis, 4.26 grams (g) tetrapropylammonium bromide (TPA) and 0.7407 g ammonium fluoride was dissolved in 72 ml of water and stirred well for 15 minutes. Then, 12 g fumed silica was added and stirred well until homogenized. The obtained gel was autoclaved and kept at 200° C. for 2 days. The molar composition of gel was 1 $SiO_2$: 0.08 (TPA)Br: 0.10 $NH_4F$: 20 $H_2O$. The solid products obtained were washed with water and dried at 80° C. overnight. The template was removed by calcination in air at 750° C. for 5 hours.

Example 3

Preparation of MFI-2000

In a typical synthesis, 4.26 g TPA and 0.7407 g ammonium fluoride was dissolved in 72 ml of water and stirred well for 15 minutes. 12 g fumed silica was added and stirred well until homogenized. An appropriate amount of aluminum sulfate was added and the obtained gel was autoclaved and kept at 200° C. for 2 days. The molar composition of gel was 1 $SiO_2$: 0.0005 $Al_2O_3$: 0.08 (TPA)Br: 0.10 $NH_4F$: 20 $H_2O$. The solid products obtained were washed with water and dried at 80° C. overnight. The template was removed by calcination in air at 550° C. for 5 hours.

Example 4

Preparation of $10WO_3$/Q10

$10WO_3$/CARiACT Q10 was prepared by the wet impregnation method. An aqueous solution of ammonium metatungstate $[(NH_4)6H_2W_{12}O_{40} \bullet xH_2O]$ and the commercial silica support were mixed together and dried in an oven at 110° C. for 12 hours and calcined at 550° C. for 8 hours. As shown in Table 1 as follows, the supported tungsten oxide catalyst ($10WO_3$/Q10) has a lower surface area when compared to the parent Q10 material, indicating the presence of tungsten oxide on the support.

Figure 1:
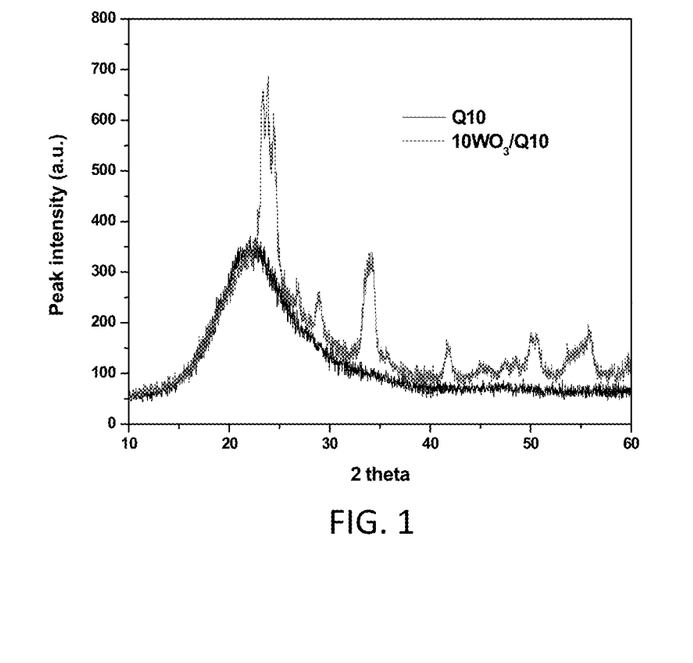
FIG. 1 is an X-ray Powder Diffraction (XRD) graph illustrating the XRD profile of a CARiACT Q10 support, and a CARiACT Q10 support impregnated with WO$_3$ at a molar ratio of silica/WO$_3$ equal to approximately 10 in accordance with one or more embodiments of the present disclosure.
Figure 2:
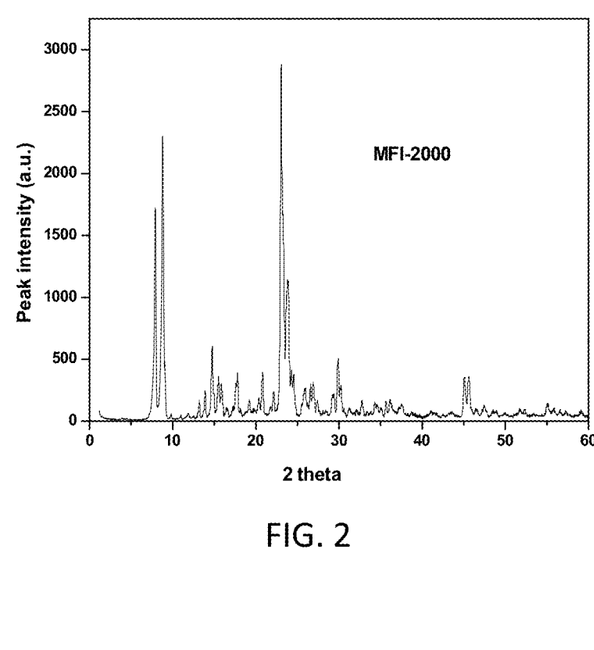
FIG. 2 is an XRD graph of a MFI-2000 catalyst.

The SEM images of CARiACT Q10 support and $10WO_3$/Q10 catalyst are shown in FIGS. 1 and 2, respectively. Both the CARiACT Q10 support and the tungsten loaded $10WO_3$/Q10 have a particle size in the range of 75-125 nm. Lack of agglomeration of tungsten oxide particles in $10WO_3$/Q10 indicates a high dispersion of tungsten oxide on the support. Referring to FIG. 2, the SEM image of MFI-2000 shows a uniform particle size distribution with crystal size of about 35-50 μm. The X, Y, and Z axis of crystal are 50 μm, 16 μm, and 3 μm, respectively.

Figure 3:
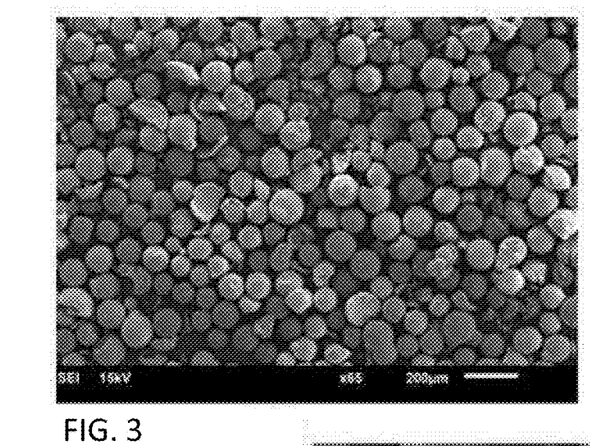
FIG. 3 is a Scanning Electron Microscopy (SEM) image of a CARiACT Q10 support.
Figure 4:
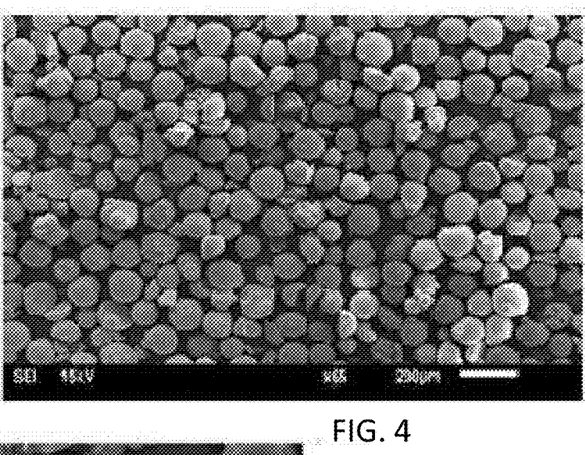
FIG. 4 is an SEM image of a CARiACT Q10 support impregnated with 10% by weight WO$_3$ in accordance with one or more embodiments of the present disclosure.
Figure 5:
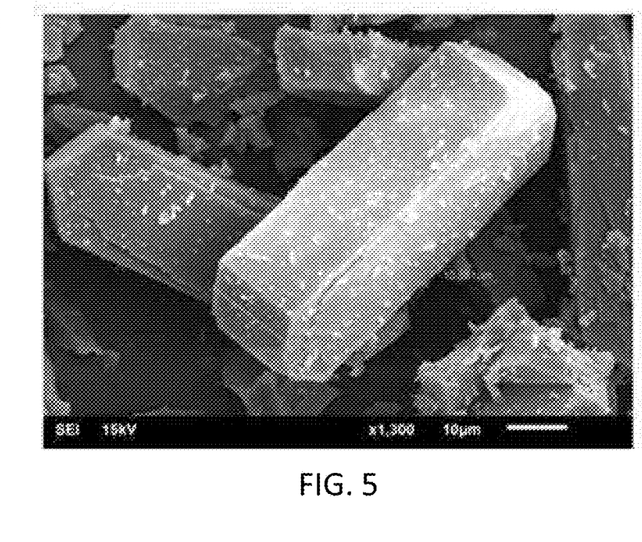
FIG. 5 is an SEM image of a of MFI-2000 catalyst.

The XRD patterns of Q10, $10WO_3$/Q10 and the MFI-2000 materials are shown in FIGS. 3-5. Referring to FIG. 4, the Q10 support shows a broad peak at 15-20° indicating the presence of amorphous silica in the material. Further referring to FIG. 4, the $10WO_3$/Q10 catalyst shows peaks at 23.09, 23.57, 24.33 and 34.01 corresponding to the crystalline phase of $WO_3$. This shows the presence of $WO_3$ species in the catalyst. As shown in FIG. 5, the XRD patterns of MFI-2000 exhibit peaks characteristic of the MFI structure in the ranges 8-9° and 22-25°. The intensity of the peak at $2\theta=8.8°$ is comparable with the peaks in the range 22-25° indicating the formation of zeolite crystals along the b-axis.

Example 5

Catalyst Properties

Table 1 includes mechanical properties of the catalysts prepared in Examples 1-4, plus MFI 280 which is prepared similarly to MFI-2000 as disclosed in Example 3.

TABLE 1

| Catalysts/Supports | BET Surface Area (m²/g) | Pore Volume (cm³/g) | Pore Size Distribution (nm) | Total acidity (mmol/g) |
|---|---|---|---|---|
| Metathesis Catalysts/Supports | | | | |
| W-SBA-15 (Si/W = 30) | 501 | 0.78 | 6.9 | 0.46 |
| CARiACT Q10 | 300 | 1.00 | 100 | |
| $10WO_3$/Q10 | 279 | 1.22 | 17.5 | 0.09 |

TABLE 1-continued

| Catalysts/Supports | BET Surface Area (m$^2$/g) | Pore Volume (cm$^3$/g) | Pore Size Distribution (nm) | Total acidity (mmol/g) |
|---|---|---|---|---|
| Cracking Catalysts | | | | |
| MFI-280 | 400 | 0.23 | 2.0 | 0.07 |
| MFI-2000 | 367 | 0.19 | 2.0 | 0.01 |
| Silicalite-1 | 348 | 0.23 | 2.0 | Not detected |

Example 6

Catalyst Performance of W-SBA-15 with Cracking Catalysts

The prepared catalysts from Examples 1-4 were tested for their activity and selectivity to butene metathesis reaction in a fixed bed continuous flow reactor (ID 0.25 in, Autoclave Engineers Ltd.) at atmospheric pressure. A fixed amount of catalyst samples, 1 ml of each catalyst type (with a total of 2 ml) was packed in the reactor tube with silicon carbide on top and bottom of the reactor. The catalysts were pretreated under N$_2$ at 550° C. for 1 hour. All reactions were carried out at a temperature of 550° C., a GHSV (gas hourly space velocity) of 900 h$^{-1}$, and atmospheric pressure using 2-butene (5 milliliters/minutes (ml/min)) as feed with nitrogen as diluent (25 ml/min). The quantitative analysis of the reaction products were carried out on-line using Varian gas chromatograph with flame ionization detector (FID) (Varian 450-GC), equipped with GasPro porous layer open tubular column.

Table 2 indicates the catalytic performances of cracking catalysts MFI-280 and MFI-2000 individually and in a combination (dual) mode with catalyst W-SBA-15(30) in the metathesis and cracking reaction of 2-butene (Reaction temperature: 550° C., atmospheric pressure, GHSV of 900 h$^{-1}$). It can be seen that the combination of W-SBA-15 metathesis catalyst with downstream MFI-2000 cracking catalyst offered the highest yields of propylene.

TABLE 2

| Product Component | MFI-280 | W-SBA-15(30) MFI-280 | MFI-2000 | W-SBA-15(30) MFI-2000 |
|---|---|---|---|---|
| Conversion 2-C$_4$ (%) | 95.67 | 94.16 | 93.72 | 91.00 |
| Yield (mol %) | | | | |
| C$_2$= | 30.53 | 29.61 | 30.29 | 22.99 |
| C$_3$= | 29.14 | 33.19 | 38.98 | 45.46 |
| 1-C$_4$= | 1.82 | 2.50 | 2.91 | 4.21 |
| Isobutylene | 3.92 | 5.72 | 5.96 | 8.52 |
| C$_5$= | 1.81 | 2.88 | 2.31 | 3.98 |
| C$_6$= | 0.00 | 0.00 | 0.00 | 0.32 |

Table 3 shows the catalytic performance of individual catalyst W-SBA-15(30) and a dual W-SBA-15(30)/silicalite-1 catalyst in the metathesis and cracking reaction of 2-butene (Reaction temperature: 550° C., atmospheric pressure, GHSV of 900 hr$^{-1}$).

TABLE 3

| Product Component | W-SBA-15(30) | W-SBA-15(30) & Silicalite-1 |
|---|---|---|
| Conversion 2-C$_4$ (%) | 81.69 | 87.03 |
| Yield (mol %) | | |
| C$_2$= | 11.48 | 14.87 |
| C$_3$= | 35.54 | 43.58 |
| 1-C$_4$= | 8.06 | 5.80 |
| Isobutylene | 3.24 | 11.28 |
| C$_5$= | 15.05 | 8.09 |
| C$_6$= | 4.20 | 0.38 |

Example 7

Catalyst Performance of CARiACT Q10 with Cracking Catalysts

The catalyst performance was also evaluated for the CARiACT Q10 metathesis catalyst as described in Example 4. The catalytic reaction of 2-butene (1:1 mixture of trans-2-butene & cis-2-butene) was performed in a fixed-bed tubular reactor (grade 316 stainless steel tube with an ID) of 0.312 inches, OD) of 0.562 inches and a length of 8 inches), in the experiment, the reactor is charged with 2 ml of the catalyst (single-bed) previously sieved to a particle size of 0.5-1.0 mm diameter. The catalyst sample was first activated in a nitrogen stream at 550° C. for 1 hours. The flow rates of feed (2-Butene) and N$_2$ were maintained at 5.0 ml/min and 25 ml/min, respectively, during the reaction. The reaction was carried out at a temperature of 550° C. at atmospheric pressure with a GHSV (gas hourly space velocity) of 900 h and a 5 hour time-on-stream (TOS). In the case of the dual catalyst system, 1 ml of each catalyst separated with glass wool was used.

The supported tungsten oxide catalyst was tested in both the single and dual catalyst systems and the results are shown in Table 4. The highest propylene selectivity is obtained for a dual catalyst system with 10WO$_3$/Q10 at the top (T) and MFI-2000 at the bottom (B) of the reactor. When 10WO$_3$/Q10 metathesis catalyst is used in a single-bed catalyst system, a propylene (C$_3$=) yield of 31.97 mol. % and a pentene (C$_5$=) yield of 12.70 mol. % are obtained. These results indicate that the pentenes formed during metathesis of butenes are not completely cracked into propylene and ethylene. However, the 10WO$_3$/Q10(T)/MFI-2000 (B) yielded 3.37 mol. % of pentene thus indicating that most of the pentenes formed during the metathesis reaction are cracked into propylene and ethylene. Thus, there is a clear advantage of using a dual catalyst system with the cracking catalyst at the bottom of the catalyst bed. Moreover, when comparing the 10WO$_3$/Q10(T)/MFI-2000(B) with the reverse arrangement of cracking catalyst upstream of metathesis catalyst, the 10WO$_3$/Q10(T)/MFI-2000 (B) yields approximately a 4.5 mol. % increase in propylene over the MFI-2000(T)/10WO$_3$/Q10(B) while only yielding slightly less (~1.5 mol. %) ethylene (C$_2$=). Thus, propylene yield is clearly maximized by using a dual catalyst system with the cracking catalyst at the bottom of the catalyst bed.

TABLE 4

| Product Component | MFI-2000 | 10WO$_3$/Q10 | 10WO$_3$/Q10(T) MFI-2000 (B) | 10WO$_3$/Q10 mixed MFI-2000 | MFI-2000 (T) 10WO$_3$/Q10 (B) |
|---|---|---|---|---|---|
| Conversion 2-C$_4$ = (%) | 92.24 | 70.96 | 86.35 | 87.01 | 86.2 |
| Yield (mol %) | | | | | |
| C$_2$= | 29.39 | 7.95 | 23.01 | 24.76 | 24.85 |
| C$_3$= | 37.56 | 31.97 | 45.64 | 43.77 | 41.09 |
| 1-C$_4$= | 2.80 | 10.83 | 4.78 | 4.87 | 4.98 |
| Isobutylene | 5.72 | 2.20 | 9.83 | 10.01 | 11.04 |
| C$_5$= | 2.25 | 12.70 | 3.37 | 3.52 | 3.59 |
| C$_6$= | 0.00 | 2.17 | 0.00 | 0.00 | 0.00 |

Calculation Methodologies

The surface area of the samples was measured by nitrogen adsorption at 77 K using AUTOSORB-1 (Quanta Chrome). Before adsorption measurements, samples (ca. 0.1 g) were heated at 220° C. for 2 hours under nitrogen flow. The nitrogen adsorption isotherms of catalysts were measured at liquid nitrogen temperature (77 K). The surface areas and pore size distributions were calculated by the Brunauer Emmett-Teller (BET) method and the Barrett-Joyner-Halenda (BJH) method, respectively. The total pore volume was estimated from the amount of N2 adsorbed at P/P0=0.99. Barret E P, Joyner L J, Halenda P H, J. Am, Chem. Soc. 7:3 (1951) 373-380.

The zeolite samples were characterized by XRD with a Rigaku Mini-flex II system using nickel filtered CuKα radiation (λ=1.5406 Å, 30 kV and 15 mA). The XRD patterns were recorded in static scanning mode from 1.2-50° (2θ) at a detector angular speed of 2° min$^{-1}$ with a step size of 0.02°.

SEM images were measured with a JEOL JSM-5800 scanning microscope at a magnification of 7000. Before taking SEM photographs, the samples were loaded on a sample holder, held with conductive aluminum tape, and coated with a film of gold in a vacuum with a Cressington sputter ion-coater for 20 seconds with 15 milliAmpere (mA) current.

It should now be understood that various aspects of the systems and methods of making propylene with the dual catalysts are described and such aspects may be utilized in conjunction with various other aspects.

In a first aspect, the disclosure provides a process for production of propylene comprising providing a dual catalyst system comprising a mesoporous silica catalyst impregnated with metal oxide, and a mordenite framework inverted (MFI) structured silica catalyst downstream of the mesoporous silica catalyst. The mesoporous silica catalyst includes a pore size distribution of about 2.5 urn to about 40 nm and a total pore volume of at least about 0.600 cm$^3$/g. The MFI structured silica catalyst includes total acidity of 0.001 mmol/g to 0.1 mmol/g. The process also comprises producing propylene from a stream comprising butene via metathesis and cracking by contacting the stream comprising butene with the dual catalyst system, where the stream comprising butene contacts the mesoporous silica catalyst before contacting the MFI structured silica catalyst.

In a second aspect, the disclosure provides a process of the first aspect, in which the mesoporous silica catalyst support is produced via wet impregnation or hydrothermal synthesis.

In a third aspect, the disclosure provides a process of either the first or second aspects, in which the butene stream comprises 2-butene, and optionally one or more of 1-butene, trans-2-butene, and cis-2-butene.

In a fourth aspect, the disclosure provides a process of any one of the first through third aspects, in which the mesoporous silica catalyst catalyzes isomerization of 2-butene to 1-butene followed by cross-metathesis of 2-butene and 1-butene into a metathesis product stream comprising propylene, and the MFI structured silica catalyst is a cracking catalyst which produces propylene from C$_4$ and C$_5$ olefins in the metathesis product stream.

In a fifth aspect, the disclosure provides a process of any one of the first through fourth aspects, in which the metal oxide of the mesoporous silica catalyst comprises one or more oxides of molybdenum, rhenium, tungsten, or combinations thereof.

In a sixth aspect, the disclosure provides a process of any one of the first through fifth aspects, in which the metal oxide of the mesoporous silica catalyst is tungsten oxide (WO$_3$).

In a seventh aspect, the disclosure provides a process of any one of the first through sixth aspects, in which the mesoporous silica catalyst has a molar ratio for silica/tungsten oxide of about 5 to about 60.

In an eighth aspect, the disclosure provides a process of any one of the first through seventh aspects, in which the mesoporous silica catalyst includes a pore size distribution of from about 2.5 nm to 20 nm.

In a ninth aspect, the disclosure provides a process of any one of the first through eighth aspects, in which the mesoporous silica catalyst has a surface area of about 250 m$^2$/g to about 600 m$^2$/g.

In a tenth aspect, the disclosure provides a process of any one of the first through ninth aspects, in which the MFI structured silica catalyst is free of acidity modifiers selected from the group consisting of rare earth modifiers, phosphorus modifiers, potassium modifiers, and combinations thereof.

In an eleventh aspect, the disclosure provides a process of any one of the first through tenth aspects, in which the mesoporous silica catalyst has a particle size of about 20 nm to about 200 nm.

In a twelfth aspect, the disclosure provides a process of any one of the first through eleventh aspects, in which the mesoporous silica catalyst has an individual crystal size ranging from about 10 to about 40 μm.

In a thirteenth aspect, the disclosure provides a process of any one of the first through twelfth aspects, in which the MFI structured silica catalyst is alumina free.

In a fourteenth aspect, the disclosure provides a process of any one of the first through thirteenth aspects, in which the MFI structured silica catalyst is alumina free or alumina containing.

In a fifteenth aspect, the disclosure provides a process of any one of the first through fourteenth aspects, in which the MFI structured silica catalyst has a molar ratio of silica to alumina of about 200 to about 3000.

In a sixteenth aspect, the disclosure provides a process of any one of the first through fifteenth aspects, in which the MFI structured silica catalyst has a molar ratio of silica to alumina of about 200 to about 3000.

In a seventeenth aspect, the disclosure provides a process of any one of the first through sixteenth aspects, in which the MFI structured silica catalyst has a surface area of at about 300 m$^2$/g to about 425 m$^2$/g.

In an eighteenth aspect, the disclosure provides a process of any one of the first through seventeenth aspects, in which the MFI structured silica catalyst has a pore size distribution of from about 1.5 nm to 3 nm and a pore volume of at about 0.1 cm$^3$/g to about 0.3 cm$^3$/g.

In a nineteenth aspect, the disclosure provides a process of any one of the first through eighteenth aspects, in which the MFI structured silica catalyst has a crystal size of about 10 μm to about 40 μm.

In a twentieth aspect, the disclosure provides a process of any one of the first through twentieth aspects, in which the contact between the butene and the catalyst occurs at a space hour velocity of about 300 to about 1200 h$^{-1}$.

In a twenty-first aspect, the disclosure provides a process of any one of the first through twentieth aspects, in which the contact between the butene and the catalyst is at a temperature of about 300 to about 600° C.

In a twenty-second aspect, the disclosure provides a process of any one of the first through twenty-first aspects, in which the contact between the butene and the catalyst is at a pressure of about 1 to about 10 bars.

In a twenty-third aspect, the disclosure provides a process of any one of the first through twenty-second aspects, in which the process achieves at least an 85 mol. % conversion of butene and a propylene yield in mol. % of the at least 45%.

In a twenty-fourth aspect, the disclosure provides a process of any one of the first through twenty-third aspects, in which the process achieves at least an 85 mol. % conversion of butene and a propylene yield in mol. % of at least 45%.

In a twenty-fifth aspect, the disclosure provides a process of any one of the first through twenty-fourth aspects, in which the process achieves a yield of at least a 15 mol. % ethylene.

In a twenty-sixth aspect, the disclosure provides a process of any one of the first through twenty-fifth aspects, in which the process achieves a yield of at least 20 mol. % ethylene and a propylene yield in mol. % of the at least 45%.

In a twenty-seventh aspect, the disclosure provides a dual catalyst system for producing propylene from butene, which may be utilized in the process of process of any one of the first through twenty-sixth aspects, where the dual catalyst system comprising a metathesis catalyst zone and a cracking catalyst zone downstream of the metathesis catalyst zone. The metathesis catalyst zone comprises mesoporous silica, catalyst impregnated with metal oxide, where the mesoporous silica catalyst includes a pore size distribution of at least about 2.5 nm to about 40 nm and a total pore volume of at least about 0.600 cm$^3$/g. The cracking catalyst zone comprises a mordenite framework inverted (MFI) structured silica catalyst, where the MFI structured silica catalyst includes a pore size distribution of at least 1.5 nm to 3 nm, and a total acidity of 0.0 mmol/g to 0.1 mmol/g.

In a twenty-eighth aspect, the disclosure provides a dual catalyst system of the the twenty-seventh aspect, in which the metathesis catalyst zone and the cracking catalyst zone are disposed in one reactor.

In a twenty-ninth aspect, the disclosure provides a dual catalyst system of any one of the twenty-seventh or twenty-eighth aspects, in which the metathesis catalyst zone is disposed in a first reactor and the cracking catalyst zone is disposed in a second reactor downstream of the first reactor.

In a thirtieth aspect, the disclosure provides a dual catalyst system of the thirtieth aspect, in which there is a conduit between the first reactor and the second reactor.

In a thirty-first aspect, the disclosure provides a dual catalyst system of any one of the twenty-seventh through thirtieth aspects, in which the mesoporous silica catalyst has a molar ratio for silicalmetal oxide of about 10 to about 50.

In a thirty-second aspect, the disclosure provides a dual catalyst system of any one of the twenty-seventh through thirty-first aspects, in which the metal oxide of the mesoporous silica catalyst is tungsten oxide (WO$_3$).

In a thirty-third aspect, the disclosure provides a dual catalyst system of any one of the twenty-seventh through thirty-second aspects, in which the MFI structured silica catalyst is alumina free or comprises alumina.

In a thirty-fourth aspect, the disclosure provides a dual catalyst system of any one of the twenty-seventh through thirty-third aspects, in which the MFI structured silica catalyst has a molar ratio of silica to alumina of about 200 to about 3000.

In a thirty-fifth aspect, the disclosure provides a dual catalyst system of any one of the twenty-seventh through thirty-fourth aspects, in which the MFI structured silica catalyst is free of acidity modifiers selected from the group consisting of rare earth modifiers, phosphorus modifiers, potassium modifiers, and combinations thereof.

It should be apparent to those skilled in the art that various modifications and variations can be made to the described embodiments without departing from the spirit and scope of the claimed subject matter. Thus it is intended that the specification cover the modifications and variations of the various described embodiments provided such modification and variations come within the scope of the appended claims and their equivalents.

What is claimed is:

1. A dual catalyst system for producing propylene from butene, the dual catalyst system comprising a metathesis catalyst zone and a cracking catalyst zone where:
    the metathesis catalyst zone comprises mesoporous silica catalyst impregnated with metal oxide;
    the cracking catalyst zone comprises a mordenite framework inverted (MFI) structured silica catalyst;
    the cracking catalyst zone is directly downstream of the metathesis catalyst zone; and
    the cracking catalyst zone is in fluidic communication with the metathesis catalyst zone.

2. The dual catalyst system of claim 1 where the metathesis catalyst zone and the cracking catalyst zone are disposed in one reactor.

3. The dual catalyst system of claim 2 in which at least a portion of the MFI structured silica catalyst is in contact with at least a portion of the mesoporous silica catalyst impregnated with metal oxide.

4. The dual catalyst system of claim 1 where the metathesis catalyst zone is disposed in a first reactor and the cracking catalyst zone is disposed in a second reactor directly downstream of the first reactor.

5. The dual catalyst system of claim 4 further comprising a direct conduit between the first reactor and the second reactor.

6. The dual catalyst system of claim 1 where the metal oxide of the mesoporous silica catalyst comprises one or more oxides of molybdenum, rhenium, tungsten, or combinations thereof.

7. The dual catalyst system of claim 1 where the mesoporous silica catalyst has a molar ratio for silica/metal oxide of 10 to 50.

8. The dual catalyst system of claim 1 where the metal oxide of the mesoporous silica catalyst is tungsten oxide ($WO_3$).

9. The dual catalyst system of claim 1 in which the mesoporous silica catalyst includes a pore size distribution of at least 2.5 nm to 40 nm.

10. The dual catalyst system of claim 1 in which the mesoporous silica catalyst includes a total pore volume of at least 0.600 $cm^3/g$.

11. The dual catalyst system of claim 1 in which the MFI structured silica catalyst includes a pore size distribution of at least 1.5 nm to 3 nm.

12. The dual catalyst system of claim 1 in which the MFI structured silica catalyst includes a total acidity of 0.001 mmol/g to 0.1 mmol/g.

13. The dual catalyst system of claim 1 where the MFI structured silica catalyst is alumina free.

14. The dual catalyst system of claim 1 where the MFI structured silica catalyst comprises alumina.

15. The dual catalyst system of claim 9 where the MFI structured silica catalyst has a molar ratio of silica to alumina of 200 to 3000.

16. The dual catalyst system of claim 1 where the MFI structured silica catalyst is free of acidity modifiers selected from the group consisting of rare earth modifiers, phosphorus modifiers, potassium modifiers, and combinations thereof.

\* \* \* \* \*

UNITED STATES PATENT AND TRADEMARK OFFICE
CERTIFICATE OF CORRECTION

PATENT NO. : 10,583,423 B2
APPLICATION NO. : 16/039983
DATED : March 10, 2020
INVENTOR(S) : Al-Khattaf et al.

It is certified that error appears in the above-identified patent and that said Letters Patent is hereby corrected as shown below:

In the Specification

In Column 2, Line 8, delete "a," and insert --a--, therefor.

In Column 4, Line 2, delete "4.5 run," and insert --4.5 nm,--, therefor.

In Column 5, Line 52, delete "less than less than" and insert --less than--, therefor.

In Column 14, Line 2, delete "the the" and insert --the--, therefor.

In Column 14, Line 16, delete "silicalmetal" and insert --silica/metal--, therefor.

Signed and Sealed this
Seventh Day of July, 2020

Andrei Iancu
*Director of the United States Patent and Trademark Office*